United States Patent
Melles

(10) Patent No.: US 6,720,314 B1
(45) Date of Patent: Apr. 13, 2004

(54) USE OF A VITAL DYE FOR FACILITATING SURGICAL PROCEDURES FOR CATARACT EXTRACTION

(76) Inventor: Gerrit Reinold J. Melles, H. A. Maaskantstraat 31, 3071 MJ Rotterdam (NL)

( * ) Notice: Subject to any disclaimer, the term of this patent is extended or adjusted under 35 U.S.C. 154(b) by 0 days.

(21) Appl. No.: 09/708,386

(22) Filed: Nov. 8, 2000

Related U.S. Application Data

(63) Continuation of application No. PCT/NL99/00284, filed on May 7, 1999.

(30) Foreign Application Priority Data

May 8, 1998 (EP) .............................. 98201542

(51) Int. Cl.[7] ...................... A61K 31/655; A61B 10/00
(52) U.S. Cl. ...................... 514/150; 514/150; 514/657; 514/728; 424/9.6; 424/9.61; 600/558; 604/28
(58) Field of Search ................. 424/9.6, 9.61; 604/28; 600/558; 514/727

(56) References Cited

U.S. PATENT DOCUMENTS

| | | | | |
|---|---|---|---|---|
| 4,350,676 A | | 9/1982 | Laties et al. ............ | 424/7 |
| 4,778,825 A | * | 10/1988 | Smith et al. ............ | 514/669 |
| 6,186,148 B1 | * | 2/2001 | Okada ............ | 128/898 |
| 6,367,480 B1 | * | 4/2002 | Coroneo ............ | 128/898 |
| 6,533,769 B2 | * | 3/2003 | Holmen ............ | 604/521 |

OTHER PUBLICATIONS

Horiguchi et al, Arch Ophthalmol. 1998; 116: 535–537.*
Gimbel et al., "Development, advantages, and methods of the continuous circular capsulorhexis technique," *J. Cataract Refract Surg.*, 16:31–37 (1990).
Norn, "Vital Staining of Corneal Endothelium in Cataract Extraction," *Acta Ophthalmologica*, 49:725–733 (1971).
Norn, "Per Operative Trypan Blue Vital Staining of Corneal Endothelium," *Acta Ophthalmologica*, 58:550–555 (1980).
Solomon et al., "Protective Effect of the Anterior Lens Capsule during Extracapsular Cataract Extraction," *Ophthalmology*, 96(5):591–597 (1989).
Taniuchi, "Intraocular Penetration of Trypan Blue and of Colloidal Carbon Administered by IntraTenon's Capsulary Injection," (with English abstract) *Folia Ophthalmol*, (Dept. of Ophthalmol., Jikei Univ. School of Med., Tokyo, Japan) 32:343–350 (1981).

* cited by examiner

*Primary Examiner*—Russell Travers
*Assistant Examiner*—Shahnam Sharareh
(74) *Attorney, Agent, or Firm*—Banner & Witcoff, Ltd.

(57) ABSTRACT

Methods for performing a capsulorhexis are disclosed wherein a dye is used to stain a lens capsule of an eye. The dye is capable of staining tissue without diffusing through the tissue. Compositions including dyes that are useful in the methods are also disclosed.

8 Claims, No Drawings

USE OF A VITAL DYE FOR FACILITATING SURGICAL PROCEDURES FOR CATARACT EXTRACTION

This is a continuation application of international application No. PCT/NL99/00284, filed May 7, 1999; which claims priority from European patent application no. 98201542.2, filed May 8, 1998.

The invention relates to the field of ocular surgery, in particular to surgical procedures for cataract extraction.

In the normal eye, the crystalline lens is located behind the iris, and in front of the corpus vitreum. The lens is transparent, biconvex, accounts for about 20 diopters of convergent refractive power of the eye, and it is composed of a capsule that encloses and encompasses the lens substance, i.e. the lens epithelium, the cortex, and the nucleus. A ring of zonular fibers, that extend from the ciliary body to the anterior part of the lens capsule, keeps the lens positioned within the eye.

The capsule is an elastic, type IV collagen basement membrane produced by the lens epithelial cells. The thickness of the capsule varies from 4–24 μm, with a thickness of about 14 μm at its anterior part, 24 μm at its equatorial part, and about 4 μm at its posterior part. Because of its transparency, and because its refractive index nearly equals the lens substance, the lens capsule can not be discriminated from the lens substance, except with the use of a slit-lamp at high magnification.

The lens substance may become less transparent, i.e. a cataract may develop, due to aging or to a wide variety of ocular or systemic pathological disorders or diseases. Affected portions of the lens substance may differ with the type of disorder, but in most cases the optical and/or refractive functions of the lens are compromised, for example a decreased visual acuity, a decreased contrast sensitivity, an accommodation loss, etc.

To restore the optical pathway, cataract surgery may be performed to remove the opaque lenticular mass. Although various surgical techniques are available, extracapsular cataract extraction techniques, the Blumenthal technique, or phacoemulsification are most often used. With all techniques, the anterior chamber of the eye is opened through a peripheral corneal, limbal or scleral incision, the anterior lens capsule is opened, and the lens substance is removed, while leaving the peripheral rim of the anterior lens capsule as well as the capsular equatorial and posterior portions in-situ. The empty lens capsule forms a capsular 'bag' that can be used to support a synthetic intraocular implant lens (IOL), so that an IOL is positioned 'in the bag'.

Various techniques are used to open the anterior lens capsule, i.e. the excision of a portion of the anterior lens capsule, with or without the use of a viscous or viscoelastomeric substance, for example the can-opener technique, the envelop technique, the capsulotomy, and the continuous circular capsulorhexis. To visualize the capsular defect during the opening of the capsule, the red fundus reflex, the co-axial light of an operating microscope that is reflected from the posterior pole of the eye, is commonly used. When retroillumination is absent, for example with dense cataracts, heavily pigmented fundi or a combination of both, it is often not or only hardly possible to discriminate the anterior capsule from the underlying lens tissue.

Visualization of the defect in the anterior capsule during the opening of the lens capsule is an important step in the surgical procedure, because the mechanical traction forces which the capsule can withstand during surgery, vary with the configuration of the capsular opening. For example, in phacoemulsification a continuous circular capsulorhexis is commonly performed, because a circular configuration of the capsular opening can withstand best the surgical manipulations within the lens capsule during the removal of the lens substance. Improper visualization of the anterior lens capsule during the performance of a capsulorhexis may be responsible for a risk of a radial tear toward or beyond the equator of the lens capsule, and associated complications, for example vitreous loss, or a dropped nucleus.

Furthermore, in a subsequent phase of the surgery the outline of the opening in the anterior lens capsule is often difficult to visualize. During the removal of the lens substance in phacoemulsification a useful red fundus reflex is nearly always absent, because the lenticular tissue becomes opaque. However, during phacoemulsification it still is important that the rim of the capsulorhexis is not damaged, so that the capsular integrity is maintained during the surgical manipulations within the capsule. For example, an inadvertent touch of the rim with the tip of the phacoemulsification hand piece or an overextension of the capsule during dividing the lenticular substance, may damage the rim of the capsulorhexis. Again, the damaged rim may give a greater risk of a radial tear toward the equator and associated complications, especially because the damage to the rim of the capsulorhexis may not be noticed during surgery.

During implantation of an IOL, the rim of the anterior capsule must be visualized to place the haptics of the IOL in between the anterior and posterior portions of the lens capsule. In this phase of the surgery, the anterior capsular rim can often be seen with the use of the red fundus reflex. To determine if a haptic(s) is positioned underneath the anterior capsular rim, the IOL is manipulated in such a way that the displacement of the capsular rim by the haptic or optic of the IOL indicates the position of the IOL relative to the capsule. In cases where a useful red fundus reflex is absent, as mentioned above, it becomes difficult to determine the position of the IOL relative to the capsule. Thus, there is a risk of the IOL being inserted in the area between the iris and the anterior lens capsule, for example the ciliary sulcus. Improper positioning of an IOL (that was designed to fit into the capsular bag) may be complicated by dislocation of the IOL after surgery.

In a letter to the Editor of the Journal of Cataract and Refractive Surgery (Hoffer K J, McFarland J E, "Intracameral subcapsular fluorescein staining for improved visualization during capsulorhexis in mature cataracts", J Cataract Refract Surg 1993;19:566), K. J. Hoffer and J. E. McFarland have addressed the above problems associated with the poor visibility of the anterior capsule during the performance of the capsulorhexis, in particular in the presence of a mature cataract. They suggest that the problems may be overcome by injecting a solution of fluorescein underneath the anterior chamber. During the capsulorhexis, the capsule would be better visible due to it being stained by the fluorescein dye.

Fluorescein is a dye which is capable of diffusing through various tissue structures (see e.g. Brubaker R F, "Clinical evaluation of the circulation of aqueous humor", in Tasman W, Jaeger E A, "Duane's clinical Ophthalmology", Volume 3, Chapter 46, Philadelphia, JB Lippencott Co, 1994:1–11; or Friberg T R, "Examination of the retina: principles of fluorescein angiography", in Albert D M, Jakobiec F A, "Principles and practice of ophthalmology", Volume 2, Philadelphia, WB Saunders Co, 1994;697–718.). Consequently, when used as suggested by Hoffer and McFarland, fluorescein will not only stain the anterior lens capsule, but also the material below said capsule, particularly as the fluorescein is injected underneath the anterior lens capsule. This means that both the anterior lens capsule as well as the underlying lenticular tissue are stained by the fluorescein dye. Thus, no difference in staining can be observed between the anterior capsule and the underlying tissue during the capsulorhexis, and the desired improved visibility is not, or not sufficiently, achieved.

Moreover, it was noted by Hoffer and McFarland that the sodium hyaluronate, which is used during the operation to fill the anterior chamber of the eye, may become stained and may have to be replaced with fresh sodium hyaluronate. Of course, it is undesired to have to interrupt the course of the surgical procedure to replace the gel layer.

The present invention seeks to overcome the above described problems associated with poor visibility of the lens capsule during cataract surgery. It is an object of the invention to make it possible to visually distinguish the anterior lens capsule from the underlying lenticular material, so that the configuration of an opening in the anterior lens capsule can be better monitored during surgery, for example to prevent the development of a radial tear toward or beyond the equator of the lens capsule during the performance of a capsulorhexis.

Surprisingly, it has now been found that said object may be attained by using a specific dye or mixture of dyes, which is capable of staining tissue or a tissue component, e.g. a membrane, without diffusing through said tissue or component thereof. Hence, the invention relates to a method for performing a capsulorhexis, wherein an anterior lens capsule is stained using at least one dye, which dye is capable of staining tissue without noticeably diffusing into said tissue.

In a method according to the invention, the outer surface of the anterior lens capsule is selectively stained, by which is meant that the lenticular material beneath the anterior lens capsule, is not noticeably stained. Accordingly, during the opening of the anterior lens capsule, a clear distinction can be observed between the portion of the anterior lens capsule, that is being removed, and the underlying lenticular material. This distinction facilitates the controlled opening of the anterior capsule, and reduces the risk of inadvertent damage to the capsule, for example a radial tear toward or beyond the equator of the lens.

It has been observed that the staining of the anterior lens capsule does not have a detrimental effect on the tissue with which the dye is contacted. Furthermore, it has been observed that shortly after the surgical procedure has been completed, substantially all visible traces of the dye have disappeared. Thus, a patient undergoing a cataract extraction involving a staining of the anterior lens capsule in accordance with the invention experiences no more distress or undesired side effects as when a conventional surgical procedure, not involving staining, is employed.

Furthermore, undesired staining of the intraocular structures other than the anterior lens capsule does not, or not to an adverse extent, occur. Staining of the sodium hyaluronate gel, that is applied after rinsing the dye from the anterior chamber, also does not, or not to an adverse extent, occur.

As has been mentioned above, in a method according to the invention, the anterior lens capsule is stained using a dye. An important aspect of the invention is that a dye is used which is capable of staining tissue without diffusing into or through said tissue. Suitable dyes having this capability further should have sufficient coloring, or staining capacity at concentrations which are physiologically and toxicologically acceptable. In other words, the minimum amount of dye which is necessary to provide sufficient staining for a useful coloring to be visible should so be low that no, or hardly any, adverse toxic effects occur. Preferably, the dye is not or hardly endothelial toxic. It is further preferred, that substantially no traces of the dye are present in the eye, shortly after the cataract extraction procedure has been completed. As a result, there is hardly any risk of the patient experiencing any irritation of the cornea (corneal edema) or another part of the eye.

Particularly good results have been achieved using a dye having the formula (I)

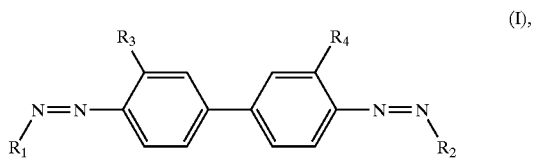

wherein $R_1$ and $R_2$ are the same or different arylgroups, and wherein $R_3$ and $R_4$ are independently chosen from hydrogen, methyl, ethyl, methoxy, amino, hydroxyl, and sulfonate. $R_1$ and $R_2$ are preferably the same and formed by substituted naphtylgroups. Preferably, the naphtylgroups are substituted with one or more of sulfonate groups, amino groups and hydroxyl groups.

In a highly preferred embodiment, the dye is chosen from the group of trypan blue, trypan red and brilliant crysyl blue. It has been found that these dyes provide a clearly visible staining at very low amounts. Also, they have an extremely advantageous toxicity profile. More preferably, the dye is trypan blue.

Of course it is also possible to use mixtures of the above dyes as long as the resulting mixture is capable of achieving a color of the anterior lens capsule which can be easily distinguished from the color of the material below said capsule.

The dye is preferably used as a physiologically compatible solution. In a particularly preferred embodiment, the dye is formulated in an aqueous salt solution, which is isotone with ocular fluid. The salt is preferably sodium chloride, sodium phosphate, potassium chloride, calcium chloride, magnesium chloride, or a combination thereof. Suitable examples are Balanced salt solution or Hartmann's lactated Ringer's solution (Nuijts R M M A, Edelhauser H F, Holley G P, "Intraocular irrigating solutions: a comparison of Hartmann's lactated Ringer's solution, BSS and BSS plus", Clin. Exp. Ophtamol., vol. 233 (1995), pp. 655–661). In accordance this embodiment, the salt concentration will be in the range of 0.8 to 1.0 wt. %, based on the weight of the solution.

It is further preferred that the solution has a neutral pH, i.e. a pH between 6.5 and 7.5. The skilled person will be able to select a suitable buffer, which has the properties to be of use in opthtalmic applications. An example of a suitable buffer is phosphate buffered NaCl, commercially available at NPBI, Emmer-Compascuum, The Netherlands.

In certain cases, depending on the desired manner of applying the dye solution to the anter lens capsule, it may be desired to formulate said solution as a dispersion, or a viscous or viscoelastomeric solution, for example hyaluronic acid (see WO-A-96/32929). It will be well within the standard expertise of the skilled person to select a suitable form for the solution. For instance, a higher viscosity may be desired in order to reduce the tension on the lenticular capsule during the capsulorhexis or to protect the cornea.

The concentration of the dye or the mixture of dyes in the solution will preferably be between 0.001 and 2 wt. %, more preferably between 0.01 and 0.1 wt. %, based on the weight of the solution. Within this range, the concentration may be adapted to the toxicity and coloring characteristics of the dye used. It is preferred that such an amount is chosen that an optimal staining effect is achieved, while at the same time the risk of possible damage to the eye or any part thereof due to the toxicity of the dye is minimized.

A method according to the invention is preferably employed as part of a surgical procedure for cataract extraction. After the eye is opened, for example by making a scleral or corneal tunnel incision, the aqeueous (ocular fluid) is aspirated and the anterior camber is filled with air. A few drops of the above described solution comprising the dye in an appropriate concentration is applied onto the anterior lens capsule. The application of the solution may be carried out by bringing a canula that is attached to a syringe containing the dye into the anterior chamber, and to inject a few drops of the dye, generally less than 1 ml, onto the anterior lens capsule.

The anterior chamber is filled with air, so that the concentration of the dye in the solution is not lowered by the aqueous. As an alternative the dye can be administered in a higher concentration into the aqueous, or a dispersion of the dye in a viscous or viscoelastomeric solution can be used.

Preferably, the excess dye is washed out by irrigating the anterior chamber, leaving a faint but clear staining of the anterior lens capsule, after which the surgery can be continued using routine techniques. The irrigation may be carried out by using Balanced salt solution or any other solution that is commonly used in intraocular surgical procedures.

After the anterior lens capsule has been stained, the capsule can be opened using routine surgical techniques. Independent of whether a red fundus reflex is present, the defect in the capsule can be observed because of the difference in color between the stained lens capsule and the exposed, grey-white lens substance. For example, the outline of capsular defect can be visualized during the creation of a capsulorhexis, during removal of the lens substance by phacoemulsification, and during implantation of an intraocular lens in subsequent phases of the surgery.

In selected cases that may have an increased risk of the development of after-cataract, a posterior capsulorhexis is made in the posterior lens capsule, before or after the implantation of an IOL. In these cases, a method according to the invention may be employed to stain the posterior lens capsule. Staining of the posterior lens capsule facilitates a controlled opening of the posterior capsule without damaging the anterior vitreous membrane.

The invention will now be elucidated by the following, non-restrictive examples.

EXAMPLE I 1 g of Trypan blue powder (Gurr, BDH Laboratory Supplies, Poole, United Kingdom) is dissolved in 1000 ml (1 liter) of Balanced salt solution (an aqueous solution of 0.9% NaCl) to obtain a concentration of 0.1 wt. % dye in solution. From the solution, 0.5 ml is drawn into a syringe, and a canula is attached to the syringe.

EXAMPLE II

An in-vivo cataract extraction procedure is carried out on a human eye. A corneal tunnel incision is made, the aqueous is aspirated and the anterior camber is filled with air. A canula that is attached to a syringe containing the dye solution prepared in accordance with Example I is brought into the anterior chamber. The tip of the canula is held against the anterior lens capsule, and a few drops of the dye solution is applied onto the anterior lens capsule. Then, the anterior chamber is flushed with Balanced salt solution (without dye), until all visible traces of the dye are washed out. A bluish staining of the anterior lens capsule was visible.

A visco-elastic substance (HPMC Ocucoat, purchased from Storz, Clear Water, Fla., USA) is injected into the anterior chamber, and with a 30 gauge needle or fine forceps, a capsulorhexis is made. The configuration of the capsulorhexis is controlled by visualization of the blue stained peripheral portion of the anterior capsule, whereas only the gray lenticular mass is seen in the area where the central portion of the anterior capsule has been excised.

After completion of the capsulorhexis, a phacoemulsification procedure is performed to remove the lenticular tissue.

What is claimed is:

1. A method for performing a capsulorhexis, comprising the steps of:

surgically opening an eye;

aspirating an ocular fluid from the eye;

filling an anterior chamber of the eye with air;

applying trypan blue onto an outer surface of a lens capsule;

producing a selectively stained lens capsule without substantially staining intraocular structures compared to the stained lens capsule;

visually distinguishing the selectively stained lens capsule from underlying lenticular material while surgically opening the lens capsule; and surgically removing lens substance.

2. A method according to claim 1, wherein the lens capsule is the anterior lens capsule.

3. A method according to claim 1, wherein the method is part of a surgical procedure for cataract extraction.

4. A method according to claim 1, wherein the trypan blue is added directly to the anterior lens capsule.

5. The method according to claim 1, wherein the trypan blue comprises a physiologically compatible solution including salt between 0.8% and 1.0% by weight.

6. The method according to claim 5, wherein the salt is selected from the group consisting of sodium chloride, sodium phosphate, potassium chloride, calcium chloride, and magnesium chloride.

7. A method according to claim 1, wherein trypan blue is applied onto a posterior lens capsule.

8. A method according to claim 7, wherein the trypan blue is added directly to the posterior lens capsule.

* * * * *